(12) United States Patent
Bayne et al.

(10) Patent No.: US 12,636,111 B2
(45) Date of Patent: May 26, 2026

(54) MULTILAYER GLOVE LOADER

(71) Applicant: Uniformed Services University of the Health Sciences, Bethesda, MD (US)

(72) Inventors: Andrew Bayne, Omaha, NE (US); Noah Smith, Pueblo, CO (US)

(73) Assignee: Uniformed Services University of the Health Sciences

( * ) Notice: Subject to any disclaimer, the term of this patent is extended or adjusted under 35 U.S.C. 154(b) by 0 days.

(21) Appl. No.: 18/883,039

(22) Filed: Sep. 12, 2024

(65) Prior Publication Data

US 2025/0082424 A1 Mar. 13, 2025

Related U.S. Application Data

(60) Provisional application No. 63/538,123, filed on Sep. 13, 2023.

(51) Int. Cl.
*A61B 42/50* (2016.01)
*A47G 25/90* (2006.01)

(52) U.S. Cl.
CPC ............ *A61B 42/50* (2016.02); *A47G 25/904* (2013.01)

(58) Field of Classification Search
CPC ........ A61B 42/40; A61B 42/50; A47G 25/904
See application file for complete search history.

(56) References Cited

U.S. PATENT DOCUMENTS

| | | | | | |
|---|---|---|---|---|---|
| 4,651,909 | A | * | 3/1987 | Banting | A47G 25/905 |
| | | | | | 223/111 |
| 4,765,520 | A | * | 8/1988 | Barton | A47G 25/905 |
| | | | | | 223/111 |
| 4,898,309 | A | * | 2/1990 | Fischer | A47G 25/904 |
| | | | | | 248/314 |
| D316,176 | S | * | 4/1991 | Fischer | D2/641 |
| 5,082,154 | A | * | 1/1992 | French | A47G 25/905 |
| | | | | | 223/111 |
| 5,826,761 | A | * | 10/1998 | Basaj | A47G 25/905 |
| | | | | | 223/111 |
| D440,740 | S | * | 4/2001 | Anctil | D2/641 |
| 6,419,131 | B1 | * | 7/2002 | Rix | A47G 25/904 |
| | | | | | 223/111 |
| 6,435,388 | B1 | | 8/2002 | Binder et al. | |
| D563,070 | S | * | 2/2008 | Palese | D32/59 |
| 7,624,455 | B1 | | 12/2009 | Bhalla | |
| 7,712,642 | B2 | | 5/2010 | Gaines et al. | |
| 8,807,402 | B2 | | 8/2014 | Backhaus et al. | |

(Continued)

FOREIGN PATENT DOCUMENTS

EP 2640206 B1 9/2013

OTHER PUBLICATIONS

Bitely C et al., "EMS Disease Exposure, Transmission, and Prevention: a Review Article," Curr Emerg Hosp Med Rep. 2019; 7(4): 135-140.

(Continued)

*Primary Examiner* — Shaun R Hurley

(57) ABSTRACT

In mass casualty (MASCAL) or similar events, combat medics often omit using body substance isolation (BSI) equipment, specifically disposable gloves, as donning gloves takes critical time away from treating patients. A multilayer glove loader and methodology of use that allows users to quickly put on multiple layers of gloves simultaneously addresses these concerns.

23 Claims, 7 Drawing Sheets

(56) References Cited

U.S. PATENT DOCUMENTS

| 8,919,620 | B2 * | 12/2014 | Taylor .................. A47G 25/905 |
| | | | 223/111 |
| 8,960,493 | B1 | 2/2015 | Dennison et al. |
| 9,925,015 | B2 | 3/2018 | Gravlee |
| 10,849,703 | B2 | 12/2020 | Backhaus et al. |
| 11,457,988 | B1 * | 10/2022 | Anderson, Jr. .... A41D 19/0093 |
| 2002/0139819 | A1 * | 10/2002 | Ferraioli .............. A47G 25/908 |
| | | | 223/111 |
| 2019/0200793 | A1 * | 7/2019 | Ivakhnyuk ......... A41D 19/0082 |

OTHER PUBLICATIONS

Chambers et al., "An Example of 3-D Printing for Expeditionary Medicine: The Air Force Retractor," Mil Med. 2020; 185 (5-6): e565-e567.

Dhinesh et al., "Study on flexural and tensile behavior of PLA, ABS and PLA-ABS materials," Materials Today: Proceedings. Jan. 2021; 45: 1175-80.

Hankscraft, "The Fast, Touchless Glove Dispenser," https://www.hankscraft.com/aeroglove/, downloaded from the internet on Aug. 27, 2024.

Hatfield, Monty, "AutoGlove makes disposable gloves reusable," https://businessnorway.com/solutions/ecocentric-innovation-autoglove-makes-disposable-gloves-reusable, Business Norway, Dec. 2, 2022.

Horning et al., "Mission engineering and prototype warfare: Operational-izing technology faster to stay ahead of the threat," Army Tank Automotive Research Development and Engineering Center. Aug. 2018; 1-7.

Kotwal et al., "Eliminating preventable death on the battlefield,". Arch Surg. 2011; 146(12): 1350-1358.

Kotwal et al . . . , "The Effect of a Golden Hour Policy on the Morbidity and Mortality of Combat Casualties," JAMA Surg. 2016; 151(1): 15-24.

Langhelm R., "S&T Helps 'Stop the Bleed'—Fast. Department of Homeland Security Science and Technology Directorate," May 2022, https://www.dhs.gov/science-andtechnology/news/2022/05/19/st-helps-stop-bleed-fast.

Sharma et al., "A review of rapid prototyping and its applications," SKIT Res J. 2020; 10(1): 89-97.

The Department of Defense, "DoD Instruction 6025.19—Individual Medical Readiness Program," Jul. 2022. https://www.esd.whs.mil/portals/54/documents/dd/issuances/dodi/602519p.pdf.

Vikke HS et al., "Compliance with hand hygiene in emergency medical services: an international observational study," Emerg Med J. 2019; 36(3): 171-175.

Viya, "Glove and Go," https://www.viya.us/, downloaded from the internet on Aug. 27, 2024.

Yu et al., "Tensile and flexural behaviors of additively manufactured continuous carbon fiber-reinforced polymer composites," Composite Structures.Oct. 2019; 225: 111147.

* cited by examiner

510
Don pre-loaded glove layers attached to multilayer glove loader tool

520
Remove the multilayer glove loader tool

530
Secure and unroll the rolled glove layers onto the hand of the user

MULTILAYER GLOVE LOADER

PRIORITY CLAIM

This application claims the benefit of provisional application Ser. No. 63/538,123 filed Sep. 13, 2023 and titled "Multilayer Glove Loader," the entire content of which is hereby incorporated by reference.

STATEMENT OF GOVERNMENT INTEREST

The invention described herein may be manufactured, used and licensed by or for the United States Government.

BACKGROUND

In mass casualty (MASCAL) events, time can be the deciding factor between life and death. Exsanguination is the most common cause of preventable death on the battlefield and other high-stress environments. Patients with profuse hemorrhage following common war-related injury mechanisms including explosions, gunshot wounds, or blunt force trauma have an average of 3-5 minutes before bleeding to death. For a combat medic, or other medical operator, these high stakes can trigger a sympathetic response including diaphoresis, loss of fine motor skills, and impaired cognitive processing. Additionally, the Golden Hour Mandate of 2009, requiring that a service member must arrive at a hospital within 60 minutes of injury, is yet another pressure imposed on deployed combat medics.

In a variety of medical environments, users such as doctors, nurses, medics, etc. rely on wearing several layers of latex gloves, one on top of each other, on their hands to efficiently conduct operations and needed care. In this way, medics can move from patient to patient or from chemical to patient by simply shedding a pair of gloves, while maintaining body substance isolation (BSI) safety. In austere, mass casualty (MASCAL) environments or chemical, biological, radiological, nuclear, and explosive (CBRNE) events, combat medics will often wear several layers of gloves and remove individual pairs as they move from patient to patient. In this way, medics protect themselves and avoid cross-contamination while preserving critical, life-saving time. However, these medics are presented with the problem of subsequent glove donning once they have run out of their original pre-mission staged glove layers. The added physiologic effects of stress in these combat environments, including diaphoretic hands, loss of fine motor skills, and impaired cognitive processing, play a major role in re-applying more layers of gloves.

Currently, layers of gloves must be loaded onto the hand one at a time, which is time very time consuming and can take additional time depending on circumstances or environments commonly found. The wearer may commonly find themselves under stress, sweating or with wet hands, for example. When these layers of gloves run out, the medics' backup is unsatisfactory; often, the medic must resort to a wadded-up ball of gloves in their pocket. This approach is slow, inefficient, and wastes valuable, life-saving time.

Therefore, in mass casualty (MASCAL) or similar events, combat medics will often omit using body substance isolation (BSI) in view of the time-sensitive nature of MASCAL and similar events and donning gloves takes critical time away from treating patients. Specifically, medics often neglect wearing disposable gloves when treating patients in these scenarios. This exclusion of gloves presents a clear danger for transmission of bloodborne and other diseases such as human immunodeficiency virus (HIV), hepatitis B virus (HBV), and hepatitis C virus (HCV). While medics and other medical personnel may be screened for such prevalent diseases, they may nonetheless be exposed to a variety of pathogens while providing care.

Moreover, it has been found that a mere 54% of prehospital providers wear disposable gloves when indicated. This represents a further increased risk to both the medic and the patient, as the ungloved hands of providers in the prehospital setting have been shown to be a vector for the development of multidrug-resistant organisms (MDROs), including methicillin-resistant *Staphylococcus aureus* (MRSA) and vancomycin-resistant *Enterococcus faecalis* (VRE). Therefore, decreasing the time required to don BSI would allow medics to not only do their job faster, but also more safely, when treating patients.

In attempts to combine efficiency and BSI compliance, many combat medics employ the strategy of wearing several layers of pre-staged gloves prior to arrival to a MASCAL. This allows for individual layers to be removed when moving from one patient to the next. However, valuable time is wasted while putting on several layers of gloves individually. Deployed medical personnel need a method that allows them to easily, readily and quickly be able to don several layers of disposable gloves.

BRIEF DESCRIPTION OF THE DRAWINGS

FIG. 3A, FIG. 3B, FIG. 3C, FIG. 3D and FIG. 3E illustrate steps for accomplishing a methodology for use of the multilayer glove loader, in accordance with various embodiments of the disclosure.

DETAILED DESCRIPTION

Figure 1A:
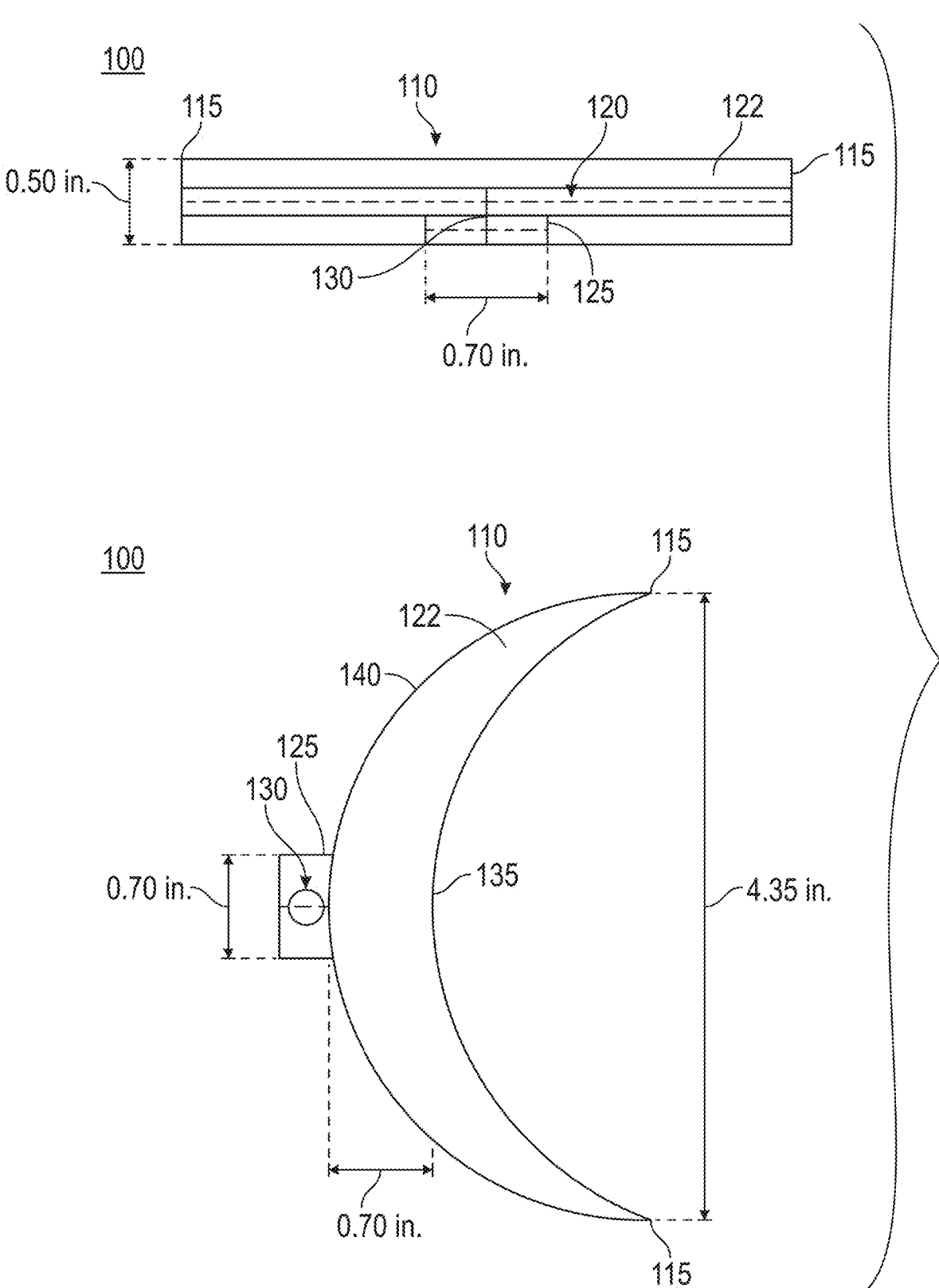
FIG. 1A, FIG. 1B, FIG. 1C and FIG. 1D show examples of the multilayer glove loader, in accordance with various embodiments of the disclosure.

Embodiments of the present disclosure will now be described with reference to the drawing figures, in which like reference numerals refer to like parts throughout.

The multilayer glove loader and methodology of use addresses the problems currently associated with loading layers of gloves onto the hand of a user one at a time. This old approach is very time consuming and can take additional time depending on circumstances or environments, including under stress, sweating, wet hands, etc. An advantage of the multilayer glove loader disclosed herein is the rapid donning of multiple layers of gloves despite difficult circumstances or situations. The crescent-shaped tool and method for using allows the user to put on multiple layers of gloves quicker, despite being under stress, a time when one has fewer fine motor skills or has wet hands. Users can replay several layers of gloves in a matter of seconds, in all kinds of difficult environments and scenarios. Additionally, the tab system of the multilayer glove loader provides to the user quick identification of the outermost glove layer to shed individual glove layers quickly.

There is no other known tool, product, system or methodology that acts as an assistive device to aid in the donning of multiple layers of disposable gloves.

In mass casualty (MASCAL) or similar events, combat medics and other users often omit using body substance isolation (BSI) equipment, specifically disposable gloves, as donning gloves takes critical time away from treating patients. The multilayer glove loader, which may be a (three-dimensional) 3D-printed tool, allows users to quickly put on multiple layers of gloves simultaneously. The durable multilayer glove loader encourage medics to quickly put on multiple layers of gloves during time-sensitive medical emergencies.

In general, the inventive devices, systems, and methods described herein advantageously allow for the efficient and rapid donning of multiple layers of disposable gloves.

In accordance with various embodiments presented herein, a multilayer glove loader is provided. The multilayer glove loader has a body having first and second opposing endpoints and a retaining element, the retaining element configured to retain two or more nested glove layers stretched over the first and second opposing endpoints and an outer surface of the body.

In accordance with various embodiments presented herein, a method of using a multilayer glove loader is provided. The method includes: a user sliding fingers of the user's hands through an opening into finger portions of two or more nested glove layers loaded onto and retained by the multilayer glove loader, the opening formed between the multilayer glove loader and a rolled portion of the two or more nested glove layers retained by the multilayer glove loader; and the user removing the multilayer glove loader from the retained rolled portion of the two or more nested glove layers by twisting towards the user a corner of the multilayer glove loader from an open end of the two or more nested glove layers towards the user.

The multilayer glove loader may be a 3D printed product, for both personal protective measures and patient body-substance isolation (BSI), that allows several layers of disposable gloves to be donned in seconds, then doffed by individual layers through use of a tab system at the wrist of the glove. This product and methodology saves critical time when users are faced with scenarios in which multiple pairs of gloves would be appropriate or desired, such as MASCAL, CBRNE, disaster relief, prehospital care, etc. When prehospital providers adhere to proper disposable glove use guidelines, there is a decreased risk of transmission of MDROs, such as MRSA and VRE, from the vector of unclean hands in locations with no readily accessible hand washing stations. In Chemical, Biological, Radiological, Nuclear, and Environmental (CBRNE) incidents, timely personal protection and reduction of cross-contamination between patients is crucial to safety. Therefore, proper BSI, especially with disposable gloves, is critical to safe care for both providers and patients. The usefulness of the product and methodology presented herein also extends to assisting users in all medical and dental services, disaster relief, lab and forensic, veterinary, janitorial, beauty, cosmetic, child-care, chemical handling, and additional industries that would benefit from using disposable gloves for personal protective equipment.

The multilayer glove loader moreover is streamlined, easy to carry by the user and suspends the gloves open such that the medic can easily don them as needed.

While use of this device and methodology on the battlefield is discussed, the disclosure is not so limited in scope and usage, being equally advantageous for utilization by emergency medical services (EMS) and other prehospital care providers. Many civilian medics have the same practice of using multiple layers of gloves when dealing with situations that require care for a high number of casualties and/or injuries. Furthermore, to aid combat medics in their meticulous pre-staging of gear prior to embarking on missions, future production of this product could be single-use and pre-packaged gloves, eliminating the need for a user to load their own gloves onto the device. Additional future research areas for the 3D-printed multilayer glove loader include uses in Chemical, Biological, Radiological, Nuclear, and Environmental (CBRNE) incidents, where timely personal protection and reduction of cross-contamination between patients is crucial to safety.

The product and methodology described herein is useful by the medical industry, medics, EMS, prehospital care, nursing, dental services, forensics, veterinary care, law enforcement, security work, disaster relief foundations, laboratory work, janitorial services, beauty services, hair dressing, cosmetic procedures, child care, safe chemical handling, plumbing, painting, commercial and industrial printing, factory workers, pest control, auto technicians and other professions which would benefit from using disposable gloves for personal protective equipment.

The multilayer glove loader is a novel device and tool designed to allow the rapid donning of several layers of gloves in a MASCAL or CBRNE event. The pocket-sized, crescent-shaped multilayer glove loader is ergonomic and ambidextrous, created to deliver up to five or more layers of preloaded gloves in seconds. The multilayer glove loader is advantageously small, taking up little storage space among other medical gear. The loader may be 3D-printed. Nearly all individuals are able to use the 3D-printed product, as it is compatible with all standard nitrile glove sizes. The final design's STL file can be transferred to any 3D printer, making it possible to print the glove loader using additional battlefield-ready materials other than onyx, such as aluminum or carbon fiber, for example.

Referring now to FIGS. 1A-1D, examples 100 of the multilayer glove loader, hereinafter glove loader, loader or tool, are shown. In FIG. 1A dimensional drawings illustrate several of the features of the glove loader 110 from top and back views. In the top view, the groove 120 along a top 122 portion or surface of the loader 110 is shown, in which nested, rolled layered gloves can rest while retained by the loader. A tab 125 with an optional hole 130 formed therein by an extruded cut is useful for removal of the glove loader once rolled gloves retained by the glove loader are placed on fingers of a user. In the front/back view of FIG. 1A, it can be seen that the loader has a generally crescent shape with an inner crescent shape 135 along a bottom of the loader and an outer crescent shape 140 along the top 122 of the loader, coming together at opposing endpoints 115 as shown. The inner and outer crescent shapes 135, 140 are generally the same arc shape, with the inner crescent shape 135 nested within the shape of the outer crescent shape as shown, though that is not a requirement. Nor is it a requirement that the loader be crescent shaped; other shapes such as oval, round, etc. could be employed. There are advantages of the crescent-shaped loader, however. The crescent shape and size means that the loader fits easily within the user's hand and around the contours of a user's hand. Moreover, the crescent shapes disposes the opposing endpoints 115 below the arc of the crescent formed along a top surface 122, providing a structure onto which rolled gloves may be stretched and retained. The dimensions of FIG. 1A are in inches and are example dimensions; other dimensions and configuration may be used if desired.

Figure 1B:
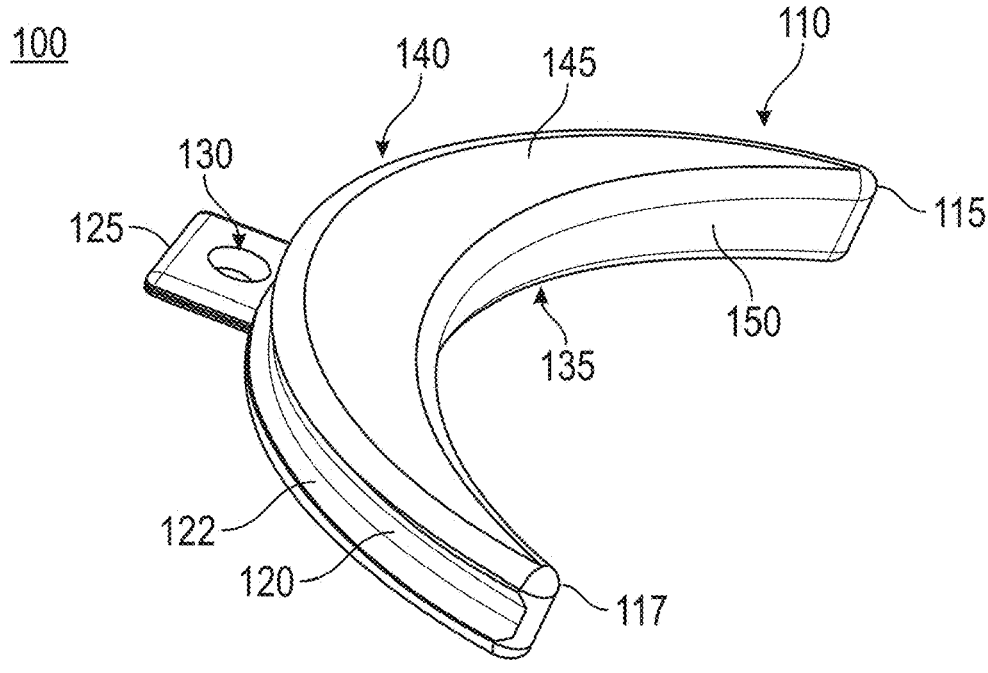

FIG. 1B provides a three-dimensional view of the multi-layer glove loader tool. In this view, the groove 120 is arranged in a top surface 122 of the body and follows the outer crescent shape 140 of the top surface 122. Also shown is the bottom surface 150 of the loader. The opposing endpoints 115 may be fitted with filets 117 to soften the edges of the endpoints 115 to prevent glove rip.

Figure 1C:
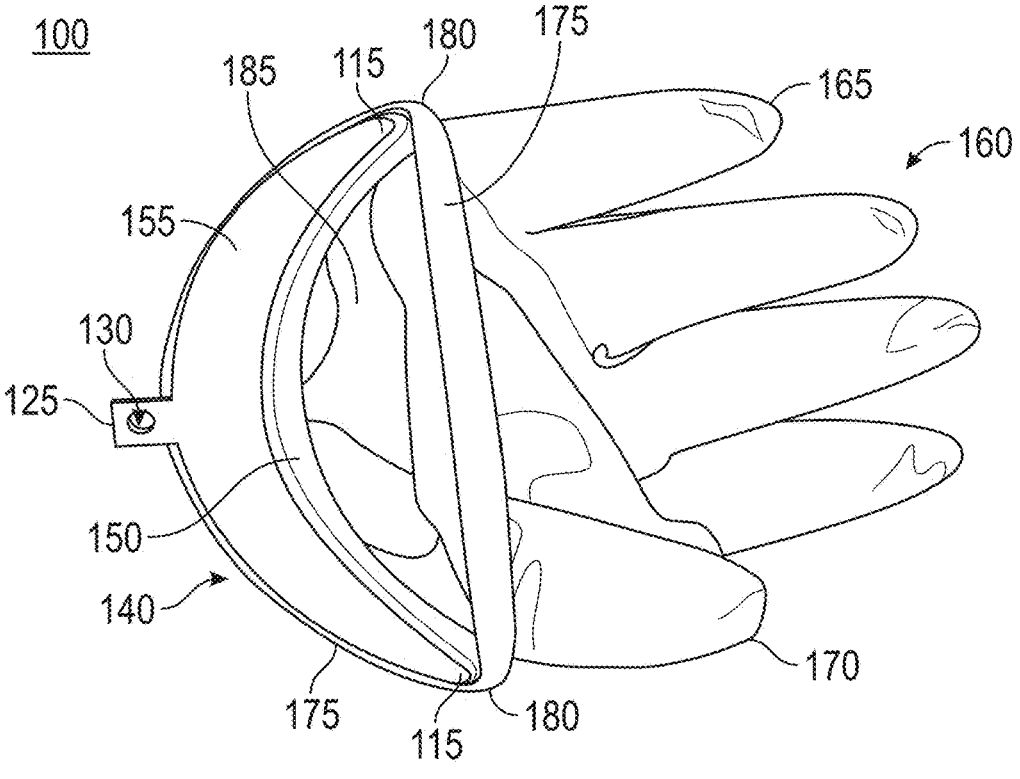
Figure 1D:
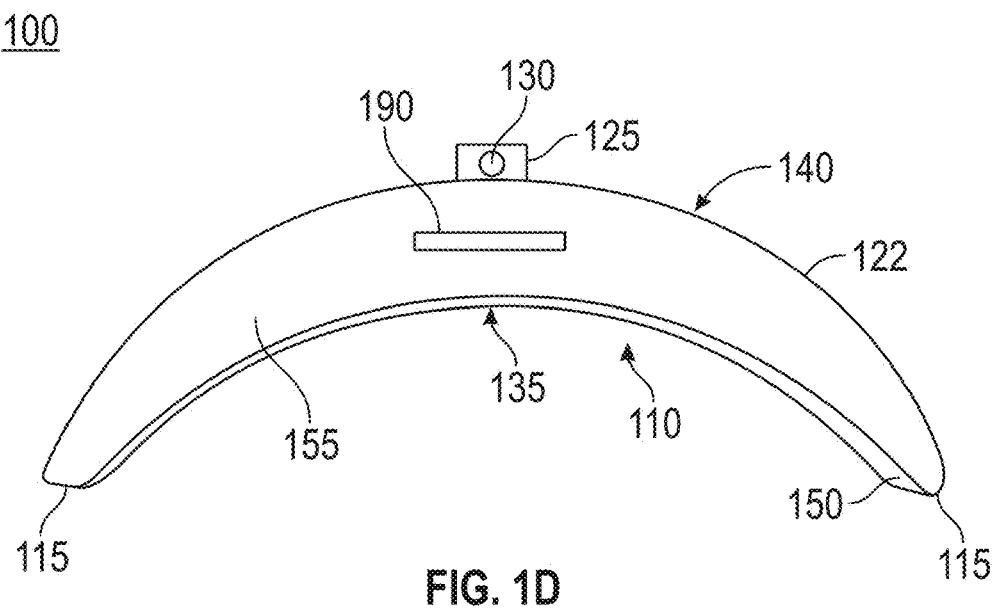

FIG. 1C illustrates a view of the backside 155 of the loader 110 in which a number of rolled, nested (layered) gloves 160 retained on the multilayer glove loader. A number of nested, layered gloves 160 are placed on the fingers 165 and operationally thumb 170 of a user. The roll 175 of the nested gloves 160 are stretched around the top surface 122 and retained in place by the groove 120 as well as around the opposing endpoints 115. The portion 180 of the roll 175 around opposing endpoints 115 is shown. Once retained in place, the inside of the innermost glove can be seen in the opening 185 formed by placement of the roll 175 about the loader 110. It is into opening 185 formed by the bottom surface 150 of the loader and the roll 175 that a user can insert their hand to don the nested and rolled layered gloves, as will be described. Though not necessary for operation, FIG. 1D illustrates an optional slit 190 formed in the back side 155 of glove loader 110 below tab 125 into which a user may blow air into the nested layered gloves to inflate the shape of the nested gloves in preparation for being donned on a hand of the user. While a rectangular slit is shown, other shapes, such a square, round, oval, etc. may be employed and are contemplated. Moreover, the slit or hole for blowing air into the nested gloves may be placed elsewhere on the body of loader 110, such as along the front side 145.

Figure 2:
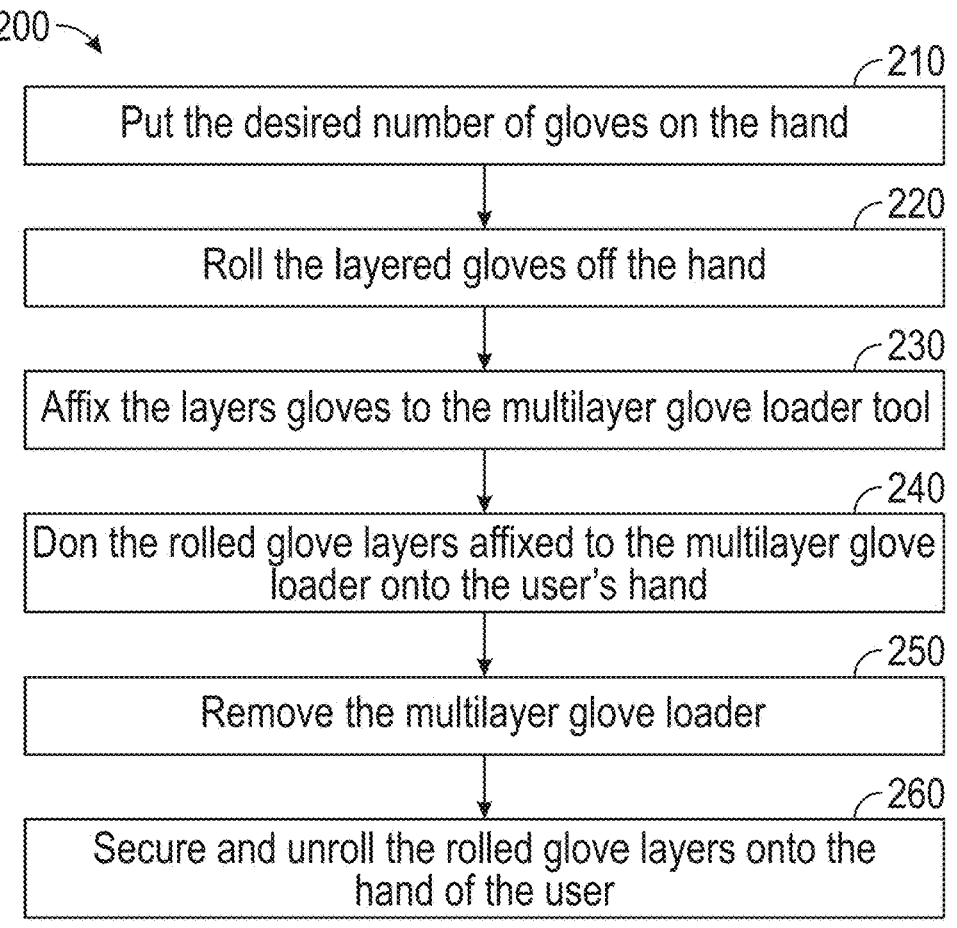
FIG. 2 illustrates a methodology for use of the multilayer glove loader, in accordance with various embodiments of the disclosure.

Referring now to flow 200 of FIG. 2, the methodology for use of the multilayer glove loader is shown. Prior to carrying out their mission, in accordance with certain embodiments, medics or other users may pre-stage loading of gloves in which multiple gloves are preloaded onto the multilayer glove loader prior to each use. This may be generally be a three step process as follows: The user puts on the desired number of gloves on their hand at 210. Next, at block 220, the user rolls the layered gloves off their hand and the roll of the layered gloves thus formed are affixed to the retaining element of the multilayer glove loader at 230. This completes a pre-stage loading stage that may be employed in preparation for use of multilayered gloves as a future time.

Next, at 240, the user can now don the rolled glove layers affixed or retained by the multilayer glove loader onto a hand. At 250, the user removes the multilayer glove loader. At 260, the rolled, nested glove layers are unrolled onto the hand of the user, ready for use, one glove at a time.

Figures 3A, 3B, 3C, 3D, 3E:
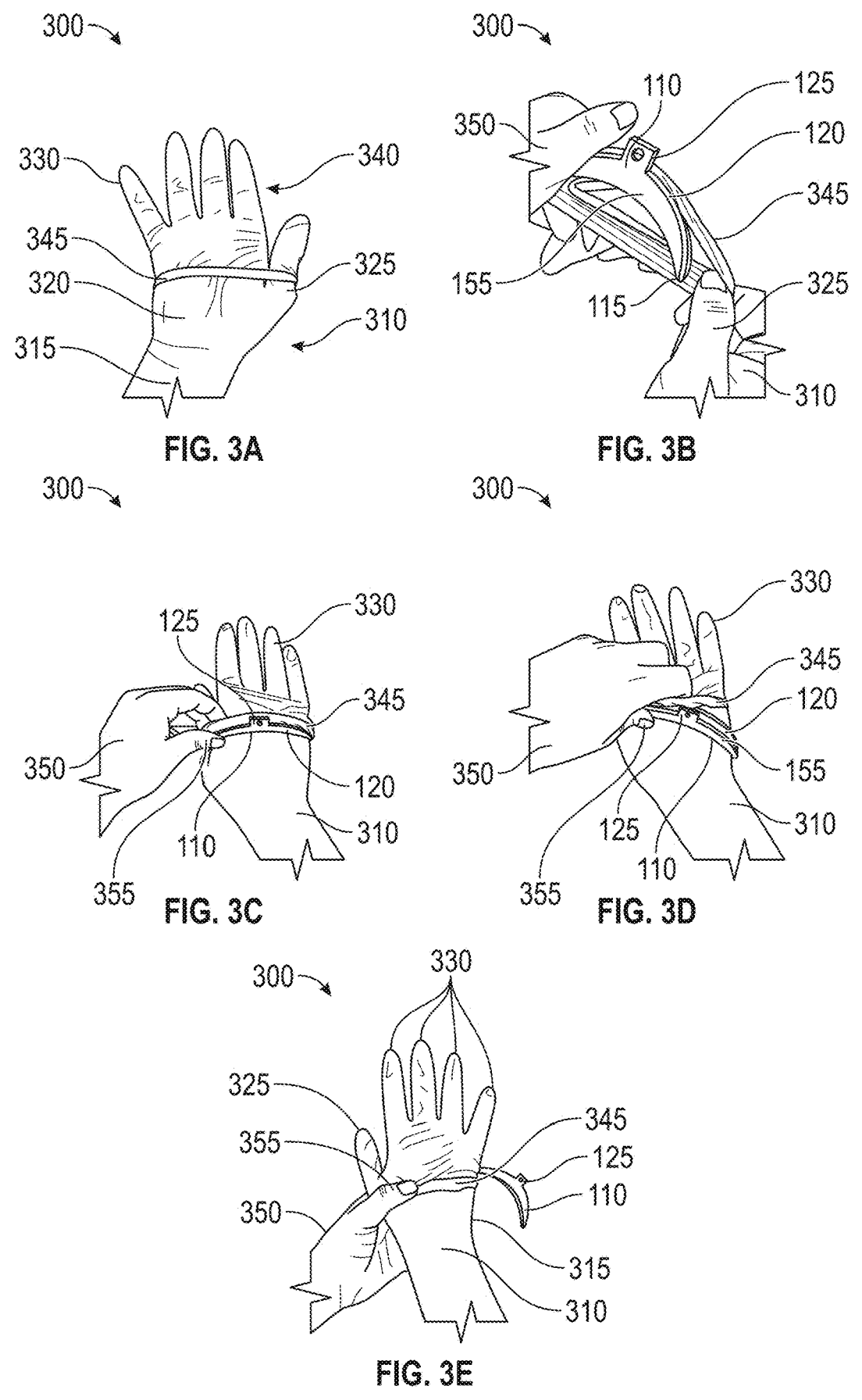

An example of this methodology 300 is illustrated in FIGS. 3A-3E. In this example, the multilayer glove loader is used to pre-load and then transfer nested, multiple glover layers onto the right hand 310 of a user. The user puts on the desired number of glove layers on the fingers 330 and thumb 325 of their right hand 310. The layered gloves 340 are then manually and tightly rolled distally from the opening of the gloves towards the fingertips of the user's fingers 330 until the hand can be removed as shown in FIG. 3A. In rolling up the layered gloves 340, a rolls 345 is formed and the right wrist 315 and right palm 320 of the user are exposed.

Next, the layered gloves are affixed (loaded onto) and releasably retained (secured) to the loader 110 in FIG. 3B: the user then places the rolled portion 345 of the nested gloves into a groove 120 on the device to hold the gloves in place, making the device ready for use in donning the layered gloves. The user uses left hand 350 and right hand/right thumb to hold the multilayer glove loader 110 so that the tab portion 125 is up and with the backside 155 of the loader 110 is facing towards the user. The right and left hands are used to secure the roll 345 into the groove 120; as shown the user's right thumb 325 stretches the roll 345 into groove 120 and around the opposing endpoints 115 as shown. As illustrated in FIG. 1C, an opening 185 is formed between the bottom surface 150 of the loader and the roll 175, 345.

For application of the gloves, the user first slides their hand through the hole formed between the roll 345 and the bottom of the multilayer glove loader 110, inserting their right fingers 330 into the four fingers of the glove while retained by loader 110 as shown in FIG. 3C. The user uses their left hand 350 and left thumb 355 to put on the rolled nested gloves onto their right hand with the right palm facing away from the user so that the back of the right hand is towards the user. The inner crescent shape 135 of the loader 110 rests comfortably on the back of the users hand, with the tab 125 of the loader 110 pointed up.

The user then frees the multilayer glove loader from the nested, layered gloves using a twisting motion of loader 110, as shown in FIG. 3D. Finally, the user's right thumb 325 is inserted into the right thumb portions of the layered gloves 340 and the layered gloves 340 are able to be unrolled down over the user's right hand 310 towards the user's right wrist 315 for coverage of the right hand 310 in FIG. 3E. The user may need to size up a glove size to accommodate for multiple glove layers to enhance dexterity and tactility. In an example consistent with that illustrated in FIGS. 3A-3E shows three layered gloves loaded onto the device. More or fewer layered gloves may be used with the multilayer glove loader.

In accordance with various embodiments, this methodology may be implemented in various ways.

Example instructions per hand in a pre-mass production example are as follows; reference is made to flow 200 of FIG. 2 and FIGS. 3A-3E:

1. User puts the desired number of layers of disposable gloves onto their hand, block 210 in FIG. 2 and as illustrated in FIG. 3A.
2. Next, the user rolls the multiple layered gloves from the wrist down to just past the thumb, block 220 and as illustrated in FIG. 3A.
3. Glove layers are removed from the user's and are now ready to be put onto the multilayer glove loader tool, as illustrated in block 220 of FIG. 2 and FIGS. 3A and 3B.
4. To load the rolled gloves onto the multilayer glove loader, block 230 of FIG. 2, the rolled portion of the glove is applied to the groove on one side of the crescent-shaped multilayer glove loader tool then stretched to the other side of the crescent endpoint 115 while keeping the rolled portion in the groove, as shown in FIG. 3B.
5. To don glove layers, the user slides their hand through the crescent, inserting their fingers into the four fingers of the glove, block 240 of FIG. 2 and as shown in FIG. 3C.

6. Next, the user removes the crescent-shaped multilayer glove loader tool from the rolled portion of the gloves, block 250 of FIG. 2 and as shown in FIG. 3D.

7. With the crescent-shaped multilayer glove loader tool now set aside, the user slides their thumb into the thumb of the glove, block 260 of FIG. 2 and as illustrated in FIG. 3E.

8. Finally, the rolled portion is now rolled back up the wrist for full coverage of the hand and ready for use, block 260 of FIG. 2 and as illustrated in FIG. 3E. Gloves may be doffed one layer at a time by grabbing the outermost glove layer by the tab 125, then removing individual layer(s) of glove(s).

To assess the time-saving capability of this multiplayer glove loader device, medical personnel having various levels of training underwent timed trials donning gloves using the multilayer glove loader method and device versus the standard method, defined as individually putting on one glove at a time. 64 timed trials were conducted, measuring the time taken to don three layers of nitrile gloves bilaterally as quickly as possible. Each individual's time using the standard method versus the same individual's time using the multilayer glove loader method was compared. From the data collected, the average time to complete the task using both methods was calculated and subsequently derived the average time saved and percent faster with and without the device. Statistical analysis of these results was performed. A two-sample t-test was performed to determine statistical significance between the two methods. All tests were performed to a significance level of 0.05.

Figure 4:
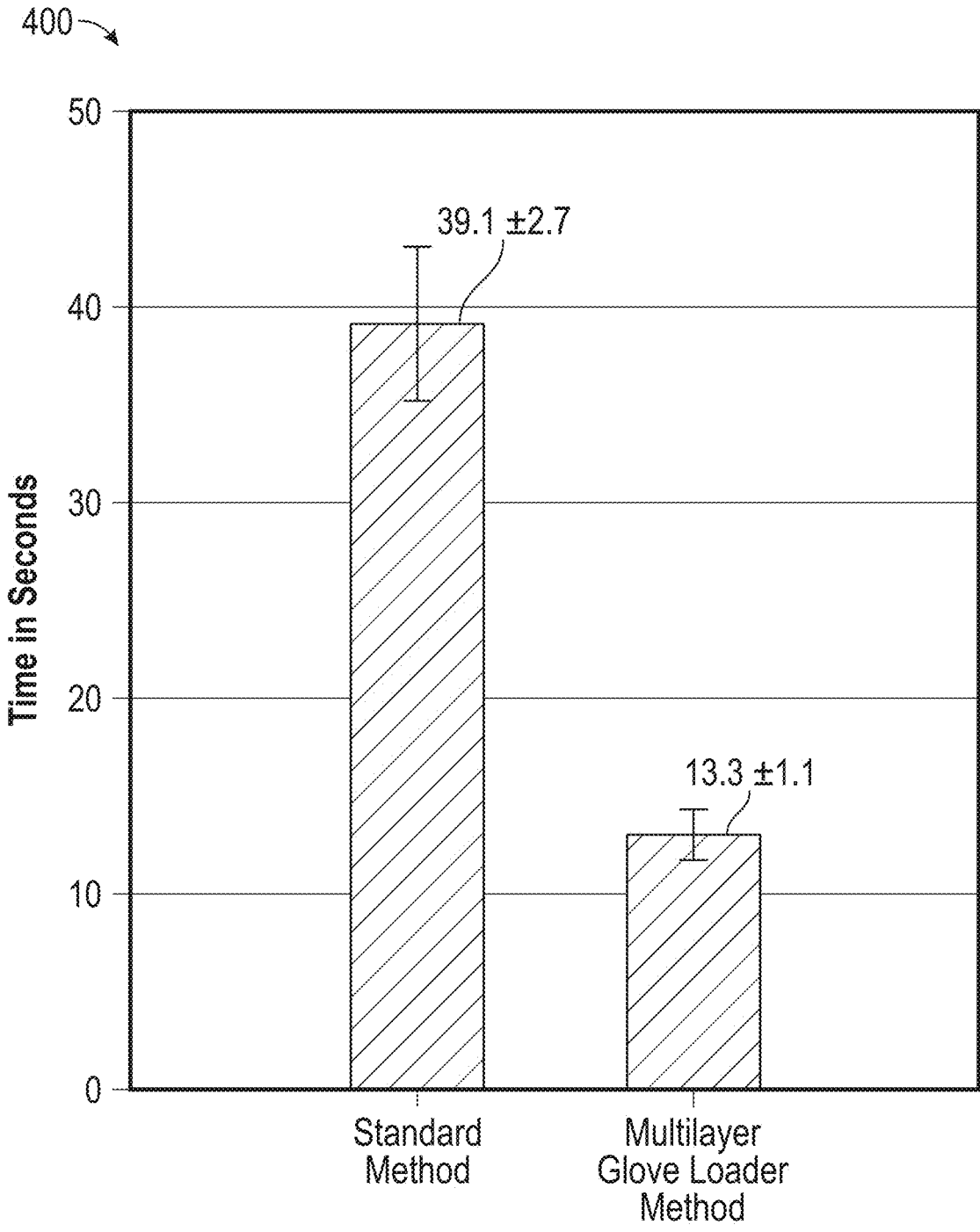
FIG. 4 depicts a bar graph that compares the average time to don gloves bilaterally with and without the multilayer glover loader, in accordance with various embodiments of the disclosure.

Time trials revealed the calculated average time to don three layers of gloves bilaterally using the multilayer glove loader method was 13.3±1.1 seconds in comparison to 39.1±2.7 seconds using the standard method. Average time saved using the multilayer glove loader method was 25.8±2.8 seconds (p<0.001), equating to a 65.0% faster average time. The bar graph 400 of FIG. 4 compares the average time to don three nitrile gloves bilaterally with and without the multilayer glover loader. This bar graph demonstrates the effectiveness of the device through a visual comparison, showing time saved.

This study revealed that the final design of the 3D-printed multilayer glove loader substantially reduced the average amount of time for a user to don three layers of nitrile gloves on both hands. This loader product device could aid medics in preserving life-saving time, while abiding by BSI standards. Protection of providers and patients through the use of BSI is critical, but often omitted, during chaotic events with a high number of casualties. The multilayer glove loader has shown promise in reducing the time barrier of donning gloves, therefore enabling and encouraging proper protection with BSI.

The multilayer glove loader device and method of use thereof substantially reduces the amount of time required for users to don BSI-compliant gloves. This will improve combat medic compliance with BSI protocols in medical environments, including during MASCAL situations, and increase available time to treat critical patients.

The multilayer glove loader described above calls for pre-staging gloves onto the loader device prior to each use. Further embodiments include prepackaged gloves on the multilayer glove loader device to allow for rapid donning, removing the need for the user to preload gloves. A multilayer glove loader pre-loaded with sterile gloves for one or both hands may be packed in sterile packaging that can be easily carried and opened as needed, ready for deployment onto one or both hands.

Example instructions with production per hand (gloves are pre-loaded in packaging); reference is made to flow 500 of FIG. 5 and FIGS. 3A-3E:

1. To don the pre-loaded glove layers pre-loaded on a crescent-shaped multilayer glove loader 110, the user slides their hand through the crescent-shaped multilayer glove loader, inserting their fingers into the four fingers of the glove, block 510 of FIG. 5. Reference may be made to FIG. 3C that shows a user sliding their right hand through a multilayer glove loader loaded with rolled up gloves.

2. Next, the user removes the crescent-shaped multilayer glove loader at block 520 from the rolled portion of the gloves by twisting one of the corners of the crescent-shaped multilayer glove loader out of the open end of the glove toward the user, as shown in FIG. 3D.

3. With the crescent-shaped multilayer glove loader tool now set aside, the user slides their thumb into the thumb of the glove at block 530 and as illustrated in FIG. 3E.

4. Finally, the rolled portion is now unrolled towards the user's wrist for full coverage of the hand and is ready for use, block 530 and as illustrated in FIG. 3E. Gloves may be doffed one layer at a time by grabbing the outermost glove layer by the tab system 125 at the wrist, then removing individual layers.

Figures 5, 6:
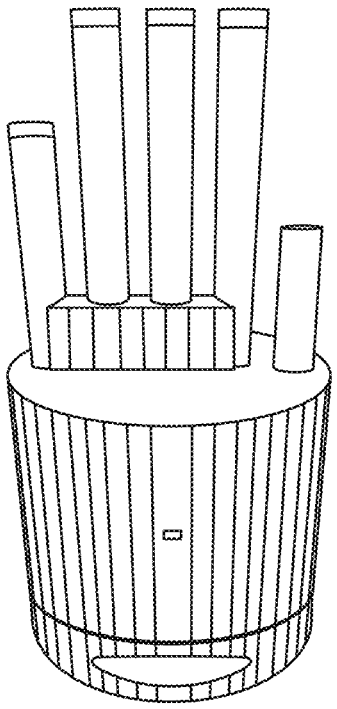
FIG. 5 illustrates a methodology for use of the multilayer glove loader, in accordance with various embodiments of the disclosure.
FIG. 6, FIG. 7 and FIG. 8 illustrate alternate embodiments of a multilayer glove loader, in accordance with various embodiments of the disclosure.
Figure 7:
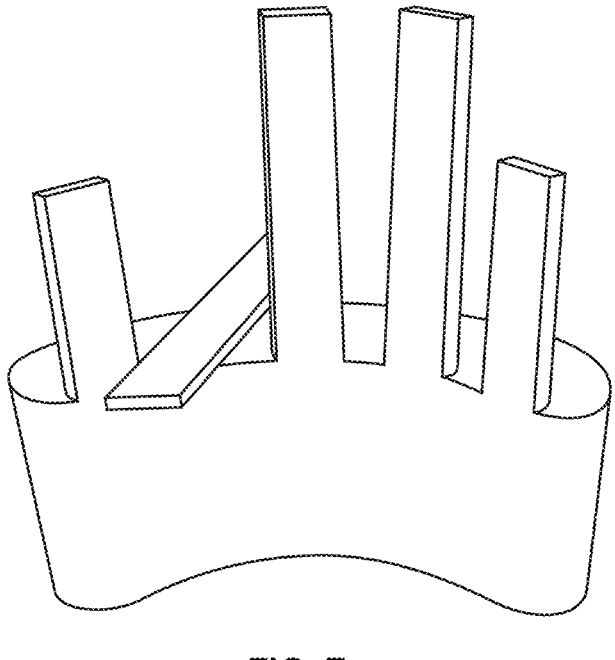
Figure 8:
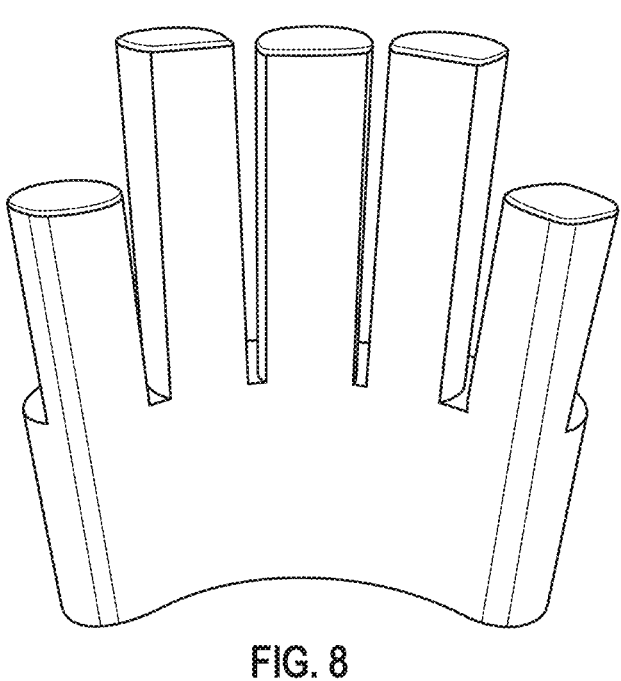

While the multilayer glove loader may be crescent-shaped as shown, other shapes may also be employed as well. A number of other embodiments in which the loader is generally hand-shaped, for example, rather than crescent-shaped are shown in FIGS. 6-8. These alternate embodiments that approximate the fingers, thumb and hand of the human body might be useful where the toughness and size advantages of the crescent-shaped tool may not be needed. These embodiments may be more bulky and large, not as easily carried, or be structurally weaker (FIG. 7) when compared to the crescent-shaped multilayer glove loader but nonetheless may be quite useful in allowing multiple layers of gloves to be donned quickly.

The multilayer glove loader may be 3D-printed with low-cost materials, such as, for example, polylactic acid (PLA) or acrylonitrile butadiene styrene (ABS). Stronger, lightweight materials such as onyx, carbon fiber, or aluminum may also be used to make the final product viable on the battlefield. A multilayer glove loader pre-loaded with sterile gloves for one or both hands may be packed in sterile packaging that can be easily carried and opened as needed, ready for deployment onto one or both hands. For example, to aid combat medics in their meticulous pre-staging of gear required prior to embarking on missions, the multilayer glove loader could be single-use and pre-packaged gloves, eliminating the need for a user to load their own gloves onto the device.

A virtual, manipulable sketch of a conceptualized prototype using SOLIDWORKS® CAD software (version 2019, Dassault Systèmes, Vélizy-Villacoublay, France) was created. A CAD-drawn model rendered on SOLIDWORKS® was converted to a stereolithography (STL) computer file to make the design compatible with additive manufacturing mediums such as 3D printers. The STL file was then transferred to a LulzBot® TAZ 6 3D Printer (Fargo Additive Manufacturing Equipment 3D, LLC, Fargo, ND, USA) and the design fabricated from cost-effective polylactic acid plastic (PLA). Next, the PLA product's ability to successfully aid the user in donning several layers of gloves simultaneously was assessed and the product's efficacy on every standard glove size (small, medium, large, and extralarge) was evaluated. This rapid prototyping method, from CAD design to PLA print for concept testing, was repeated numerous times until a final, functional product was achieved. The final design STL file was transferred to a Markforged® Onyx Pro 3D Printer (Markforged, Watertown, MS, USA) to produce a durable onyx product. Considering tensile and flexural strength constants, onyx over PLA is preferable to produce a product that would be more robust in battlefield environments.

The multilayer glove loader described herein is a crescent-shaped tool to readily, efficiently and quickly assist a user in donning multiple layers of disposable gloves onto both hands. A user may wish to consider sizing up one glove size to accommodate for multiple glove layers.

It can be seen that the multilayer glove loader is a pocket-sized, crescent-shaped, ergonomic, and ambidextrous tool, capable of delivering up to five layers, possibly more, of gloves simultaneously with any size nitrile glove. Most users preferred three to five layers of gloves for optimal dexterity and comfort because greater numbers of layers may limit mobility. The onyx 3D-printed product proved to be more durable than the PLA-printed product based on reported material stress test parameters and in practice. Onyx had higher reported tensile and flexural strengths (36.0 MPa and 81.0 MPa, respectively) versus those of PLA (20.3 MPa and 17.9 MPa, respectively).

Embodiments of the present disclosure advantageously provide a safety suture kit and methodology for using. The embodiments described above and summarized below are combinable.

In one embodiment of a multilayer glove loader, there is provided a body having first and second opposing endpoints and a retaining element, the retaining element configured to retain two or more nested glove layers stretched over the first and second opposing endpoints and an outer surface of the body.

In another embodiment of a multilayer glove loader, the retaining element is configured to retain a rolled portion of the two or more nested glove layers stretched over the first and second opposing endpoints and an outer surface of the body.

In another embodiment of a multilayer glove loader, the retaining element retains the rolled portion of the two or more nested glove layers stretched over an outer crescent shape of a top surface of the body and the first and second opposing endpoints.

In another embodiment of a multilayer glove loader, after transfer of the multilayer glove loader with retained rolled portion of two or more nested glove layers onto the hand of a user, the multilayer glove loader is configured to be removed responsive to a twisting motion of the multilayer glove loader.

In another embodiment of a multilayer glove loader, the multilayer glove loader is a crescent-shaped loader in which the first and second opposing endpoints are first and second endpoints of the crescent-shaped loader and the retaining element is a groove is formed in a crescent-shaped top of the multilayer glove loader.

In another embodiment of a multilayer glove loader, the multilayer glove loader is a crescent-shaped loader with a top surface of the multilayer glove loader having an outer crescent shape and a bottom surface of the multilayer glove loader having an inner crescent shape configured to conform to the back of a user's hand.

In another embodiment of a multilayer glove loader, a rolled portion of two or more nested glove layers stretched over the outer crescent shape of the top surface and the first and second opposing endpoints is retained by the groove formed in the crescent-shaped top surface of the body.

In another embodiment of a multilayer glove loader, an opening into which a user can insert a hand is formed by the rolled portion of the two or more nested glove layers stretched over the outer crescent shape of the top surface and the first and second opposing endpoints and retained by the groove formed in the crescent-shaped top surface of the body.

In another embodiment of a multilayer glove loader, the retaining element is a groove formed in a surface of the body.

In another embodiment of a multilayer glove loader, the multilayer glove loader is crescent-shaped in which the first and second opposing endpoints are first and second endpoints of the crescent-shaped loader and in which the groove is formed in a crescent-shaped top of the multilayer glove loader.

In another embodiment of a multilayer glove loader, a tab portion of the body is configured to remove one or more nested glove layers worn on a user's hand.

In another embodiment of a multilayer glove loader, the multilayer glove loader is crescent-shaped in which the first and second opposing endpoints are first and second endpoints of the crescent-shaped loader and in which the tab portion is formed in a crescent-shaped top of the multilayer glove loader.

In another embodiment of a multilayer glove loader, the retaining element is a groove formed in the crescent-shaped top of the multilayer glove loader.

In one embodiment of a method of using a multilayer glove loader, the method includes: a user sliding fingers of the user's hands through an opening into finger portions of two or more nested glove layers loaded onto and retained by the multilayer glove loader, the opening formed between the multilayer glove loader and a rolled portion of the two or more nested glove layers retained by the multilayer glove loader; and the user removing the multilayer glove loader from the retained rolled portion of the two or more nested glove layers by twisting towards the user a corner of the multilayer glove loader from an open end of the two or more nested glove layers towards the user.

In another embodiment of a method, further including forming the opening by stretching a rolled portion of the two or more nested glove layers over first and second opposing endpoints and an outer surface of a body of the multilayer glove loader and retaining the rolled portion of the two or more nested glove layers by a retaining element of the multilayer glove loader.

In another embodiment of a method, forming the opening includes stretching the rolled portion of the two or more nested glove layers over an outer crescent shape of a top surface of the body of the multilayer glove loader and the first and second opposing endpoints and retaining the rolled portion of the two or more nested glove layers by a groove in the crescent-shaped top surface of the body.

In another embodiment of a method, further including removing the multilayer glove loader from the two or more nested glove layers after two or more finger portions of the two or more nested glove layers are placed on two or more corresponding fingers of the user.

In another embodiment of a method, further including removing one or more of the one or more nested glove layers from the hand of the user using a tab portion of the multilayer glove loader.

In another embodiment of a method, further including pre-loading the two or more nested glove layers on the multilayer glove loader, the pre-loaded two or more nested glove layers retained by a retaining element of the multilayer glove loader.

In another embodiment of a method, the pre-loading further including stretching the rolled portion of the two or more nested glove layers over first and second opposing endpoints and an outer surface of a body of the multilayer glove loader and retaining the rolled portion of the two or more nested glove layers by the retaining element of the multilayer glove loader.

In another embodiment of a method, the retaining element is a groove in the body of the multilayer glove loader.

In another embodiment of a method, further including after removing the multilayer glove loader from the retained rolled portion of the two or more nested glove layers, the user placing a thumb in a thumb portion of the two or more nested glove layers.

Embodiments of the disclosure have been described to explain the nature of the innovation. Those skilled in the art may make changes in the details, materials, steps and arrangement of the described embodiments within the principle and scope of the disclosure, as expressed in the appended claims. While implementations of the disclosure are susceptible to embodiment in many different forms, there is shown in the drawings and will herein be described in detail specific embodiments, with the understanding that the present disclosure is to be considered as an example of the principles of the disclosure and not intended to limit the disclosure to the specific embodiments shown and described. In the description above, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," "for example," or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus, device, system, etc. may be used interchangeably in this text.

The many features and advantages of the disclosure are apparent from the detailed specification, and, thus, it is intended by the appended claims to cover all such features and advantages of the disclosure which fall within the scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A multilayer glove loader, comprising:
   a body having first and second opposing endpoints and a retaining element, the retaining element configured to retain two or more nested glove layers stretched over the first and second opposing endpoints and an outer surface of the body,
   where the multilayer glove loader is crescent-shaped in which the first and second opposing endpoints are first and second endpoints of the crescent-shaped loader.

2. The multilayer glove loader of claim 1, where the retaining element is configured to retain a rolled portion of the two or more nested glove layers stretched over the first and second opposing endpoints and an outer surface of the body.

3. The multilayer glove loader of claim 2, where the retaining element retains the rolled portion of the two or more nested glove layers stretched over an outer crescent shape of a top surface of the body and the first and second opposing endpoints.

4. The multilayer glove loader of claim 1, where the retaining element is a groove formed in a crescent-shaped top of the multilayer glove loader.

5. The multilayer glove loader of claim 4, where the multilayer glove loader is a crescent-shaped loader with a top surface of the multilayer glove loader having an outer crescent shape and a bottom surface of the multilayer glove loader having an inner crescent shape configured to conform to the back of a user's hand.

6. The multilayer glove loader of claim 4, where a rolled portion of two or more nested glove layers stretched over the outer crescent shape of the top surface and the first and second opposing endpoints is retained by the groove formed in the crescent-shaped top surface of the body.

7. The multilayer glove loader of claim 6, where an opening into which a user can insert a hand is formed by the rolled portion of the two or more nested glove layers stretched over the outer crescent shape of the top surface and the first and second opposing endpoints and retained by the groove formed in the crescent-shaped top surface of the body.

8. The multilayer glove loader of claim 1, where the retaining element is a groove formed in a surface of the body.

9. The multilayer glove loader of claim 8, where the groove is formed in a crescent-shaped top of the multilayer glove loader.

10. The multilayer glove loader of claim 1, further comprising a tab portion of the body configured to remove one or more nested glove layers worn on a user's hand.

11. The multilayer glove loader of claim 10, where the tab portion is formed in a crescent-shaped top of the multilayer glove loader.

12. The multilayer glove loader of claim 11, where the retaining element is a groove formed in the crescent-shaped top of the multilayer glove loader.

13. A multilayer glove loader, comprising:

a body having first and second opposing endpoints and a retaining element, the retaining element configured to retain two or more nested glove layers stretched over the first and second opposing endpoints and an outer surface of the body, where after transfer of the multilayer glove loader with a retained rolled portion of two or more nested glove layers onto the hand of a user, the multilayer glove loader is configured to be removed responsive to a twisting motion of the multilayer glove loader.

14. The multilayer glove loader of claim 13, where the retaining element is configured to retain the retained rolled portion of the two or more nested glove layers stretched over the first and second opposing endpoints and an outer surface of the body.

15. A method of using a multilayer glove loader, comprising:

a user sliding fingers of the user's hands through an opening into finger portions of two or more nested glove layers loaded onto and retained by the multilayer glove loader, the opening formed between the multilayer glove loader and a rolled portion of the two or more nested glove layers retained by the multilayer glove loader; and the user removing the multilayer glove loader from the retained rolled portion of the two or more nested glove layers by twisting towards the user a corner of the multilayer glove loader from an open end of the two or more nested glove layers towards the user.

16. The method of claim 15, further comprising:

forming the opening by stretching a rolled portion of the two or more nested glove layers over first and second opposing endpoints and an outer surface of a body of the multilayer glove loader and retaining the rolled portion of the two or more nested glove layers by a retaining element of the multilayer glove loader.

17. The method of claim 16, where forming the opening includes stretching the rolled portion of the two or more nested glove layers over an outer crescent shape of a top surface of the body of the multilayer glove loader and the first and second opposing endpoints and retaining the rolled portion of the two or more nested glove layers by a groove in the crescent-shaped top surface of the body.

18. The method of claim 16, further comprising removing the multilayer glove loader from the two or more nested glove layers after two or more finger portions of the two or more nested glove layers are placed on two or more corresponding fingers of the user.

19. The method of claim 15, further comprising removing one or more of the one or more nested glove layers from the hand of the user using a tab portion of the multilayer glove loader.

20. The method of claim 15, further comprising:

pre-loading the two or more nested glove layers on the multilayer glove loader, the pre-loaded two or more nested glove layers retained by a retaining element of the multilayer glove loader.

21. The method of claim 20, the pre-loading further comprising:

stretching the rolled portion of the two or more nested glove layers over first and second opposing endpoints and an outer surface of a body of the multilayer glove loader and retaining the rolled portion of the two or more nested glove layers by the retaining element of the multilayer glove loader.

22. The method of claim 21, where the retaining element is a groove in the body of the multilayer glove loader.

23. The method of claim 15, further comprising:

after removing the multilayer glove loader from the retained rolled portion of the two or more nested glove layers, the user placing a thumb in a thumb portion of the two or more nested glove layers.

* * * * *